(12) United States Patent  (10) Patent No.: US 8,449,526 B2
Snyder et al.  (45) Date of Patent: May 28, 2013

(54) TORQUEABLE SOFT TIP MEDICAL DEVICE AND METHOD OF USAGE

(75) Inventors: Edward J. Snyder, Park City, UT (US); Clark C. Davis, Holladay, UT (US); Todd H. Turnlund, Park City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 463 days.

(21) Appl. No.: 11/951,975

(22) Filed: Dec. 6, 2007

(65) Prior Publication Data

US 2008/0077119 A1  Mar. 27, 2008

Related U.S. Application Data

(63) Continuation of application No. 10/188,929, filed on Jul. 3, 2002, now abandoned.

(60) Provisional application No. 60/302,685, filed on Jul. 5, 2001.

(51) Int. Cl.
 *A61M 25/00* (2006.01)
(52) U.S. Cl.
 USPC .......................................................... 604/525
(58) Field of Classification Search
 USPC ................................................. 604/523–529
 See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |

(Continued)

FOREIGN PATENT DOCUMENTS

| | | |
|---|---|---|
| AU | 723040 | 12/1997 |
| AU | 733966 | 4/1998 |

(Continued)

OTHER PUBLICATIONS

"Mechanical Design and Systems Handbook", H.A. Rothbart, 1964, p. 33-13 (one sheet).

*Primary Examiner* — Theodore Stigell
(74) *Attorney, Agent, or Firm* — Seager, Tufte & Wickhem, LLC (57) ABSTRACT

A medical device or intravascular device, and methods of use. The devices may be tubular and may have a flexible polymer tip. The body may be nitinol and may have cuts part way through along its length to facilitate bending. The device may have a liner which may extend through the tip or form the tip. The device may have markers readily visible on an X-ray viewer during insertion. The tip may have an anti-collapsing structure and may be shaped before use to perform a medical procedure such as treating an aneurysm. The device may have a strong fiber through it for complete removal. The method may include selecting the device, bending the tip, setting the shape, and inserting the device into the patient's anatomy. The shape of the tip may be set by heating with steam and then removing a mandrel.

6 Claims, 6 Drawing Sheets

U.S. PATENT DOCUMENTS

| | | |
|---|---|---|
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Willson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Towne et al. |
| 5,063,935 A | 11/1991 | Gamble |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A * | 12/1995 | Lundquist .................. 600/373 |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |

| | | | | | | |
|---|---|---|---|---|---|---|
| 5,584,821 A | 12/1996 | Hobbs et al. | | 6,165,292 A | 12/2000 | Abrams et al. |
| 5,599,326 A | 2/1997 | Carter | | 6,171,295 B1 * | 1/2001 | Garabedian et al. .......... 604/524 |
| 5,599,492 A | 2/1997 | Engelson | | 6,171,296 B1 | 1/2001 | Chow |
| 5,601,539 A | 2/1997 | Corso, Jr. | | 6,183,410 B1 | 2/2001 | Jacobsen et al. |
| 5,605,162 A | 2/1997 | Mirzaee et al. | | 6,193,686 B1 | 2/2001 | Estrada et al. |
| 5,622,184 A | 4/1997 | Ashby et al. | | 6,197,014 B1 | 3/2001 | Samson et al. |
| 5,630,806 A | 5/1997 | Inagaki et al. | | 6,203,485 B1 | 3/2001 | Urick |
| 5,637,089 A | 6/1997 | Abrams et al. | | RE37,148 E | 4/2001 | Shank |
| 5,653,697 A * | 8/1997 | Quiachon et al. .............. 604/528 | | 6,210,396 B1 * | 4/2001 | MacDonald et al. ......... 604/529 |
| 5,656,011 A | 8/1997 | Uihlein et al. | | 6,214,042 B1 | 4/2001 | Jacobsen et al. |
| 5,658,264 A | 8/1997 | Samson et al. | | 6,228,073 B1 | 5/2001 | Noone et al. |
| 5,666,968 A | 9/1997 | Imran et al. | | 6,248,082 B1 | 6/2001 | Jafari |
| 5,666,969 A | 9/1997 | Urick et al. | | 6,251,092 B1 | 6/2001 | Qin et al. |
| 5,669,926 A | 9/1997 | Aust et al. | | 6,254,549 B1 | 7/2001 | Ramzipoor |
| 5,676,659 A | 10/1997 | McGurk | | 6,260,458 B1 | 7/2001 | Jacobsen et al. |
| 5,676,697 A | 10/1997 | McDonald | | 6,273,404 B1 | 8/2001 | Holman et al. |
| 5,682,894 A | 11/1997 | Orr et al. | | 6,273,876 B1 | 8/2001 | Klima et al. |
| 5,690,120 A | 11/1997 | Jacobsen et al. | | 6,273,879 B1 | 8/2001 | Keith et al. |
| 5,720,300 A | 2/1998 | Fagan et al. | | 6,290,656 B1 | 9/2001 | Boyle et al. |
| 5,722,609 A | 3/1998 | Murakami | | 6,296,616 B1 | 10/2001 | McMahon |
| 5,728,063 A | 3/1998 | Preissman et al. | | 6,296,631 B2 | 10/2001 | Chow |
| 5,741,429 A | 4/1998 | Donadio, III et al. | | 6,302,870 B1 | 10/2001 | Jacobsen et al. |
| 5,746,701 A | 5/1998 | Noone | | 6,325,790 B1 | 12/2001 | Trotta |
| 5,769,830 A | 6/1998 | Parker | | 6,338,725 B1 | 1/2002 | Hermann et al. |
| 5,772,609 A | 6/1998 | Nguyen et al. | | 6,346,091 B1 | 2/2002 | Jacobsen et al. |
| 5,782,809 A | 7/1998 | Umeno et al. | | 6,352,515 B1 | 3/2002 | Anderson et al. |
| 5,788,653 A | 8/1998 | Lorenzo | | 6,355,005 B1 | 3/2002 | Powell et al. |
| 5,788,654 A | 8/1998 | Schwager | | 6,355,027 B1 | 3/2002 | Le et al. |
| 5,788,707 A | 8/1998 | Del Toro et al. | | 6,368,315 B1 | 4/2002 | Gillis et al. |
| 5,792,124 A | 8/1998 | Horrigan et al. | | 6,368,316 B1 | 4/2002 | Jansen et al. |
| 5,797,856 A | 8/1998 | Frisbie et al. | | 6,375,628 B1 | 4/2002 | Zadno-Azizi et al. |
| 5,800,454 A | 9/1998 | Jacobsen et al. | | 6,375,774 B1 | 4/2002 | Lunn et al. |
| 5,807,075 A | 9/1998 | Jacobsen et al. | | 6,379,369 B1 | 4/2002 | Abrams et al. |
| 5,807,249 A | 9/1998 | Qin et al. | | 6,390,993 B1 | 5/2002 | Cornish et al. |
| 5,810,885 A | 9/1998 | Zinger | | 6,398,758 B1 | 6/2002 | Jacobsen et al. |
| 5,813,996 A | 9/1998 | St. Germain et al. | | 6,428,489 B1 | 8/2002 | Jacobsen et al. |
| 5,827,225 A | 10/1998 | Ma Schwab | | 6,428,512 B1 | 8/2002 | Anderson et al. |
| 5,827,242 A | 10/1998 | Follmer et al. | | 6,431,039 B1 | 8/2002 | Jacobsen et al. |
| 5,833,632 A | 11/1998 | Jacobsen et al. | | 6,440,088 B1 | 8/2002 | Jacobsen |
| 5,836,926 A | 11/1998 | Peterson et al. | | 6,478,778 B1 | 11/2002 | Jacobsen et al. |
| 5,843,050 A | 12/1998 | Jones et al. | | 6,488,637 B1 | 12/2002 | Eder et al. |
| 5,843,244 A | 12/1998 | Pelton et al. | | 6,491,648 B1 | 12/2002 | Cornish et al. |
| 5,851,203 A | 12/1998 | van Muiden | | 6,491,671 B1 | 12/2002 | Larson, III et al. |
| 5,895,378 A | 4/1999 | Nita | | 6,503,244 B2 | 1/2003 | Hayman |
| 5,897,537 A | 4/1999 | Berg et al. | | 6,508,803 B1 | 1/2003 | Horikawa et al. |
| 5,902,254 A | 5/1999 | Magram | | 6,524,301 B1 | 2/2003 | Wilson et al. |
| 5,902,290 A | 5/1999 | Peacock, III et al. | | 6,530,934 B1 | 3/2003 | Jacobsen et al. |
| 5,904,657 A | 5/1999 | Unsworth et al. | | 6,547,779 B2 | 4/2003 | Levine et al. |
| 5,906,618 A | 5/1999 | Larson, III | | 6,553,880 B2 | 4/2003 | Jacobsen et al. |
| 5,911,715 A | 6/1999 | Berg et al. | | 6,556,873 B1 | 4/2003 | Smits |
| 5,911,717 A | 6/1999 | Jacobsen et al. | | 6,579,246 B2 | 6/2003 | Jacobsen et al. |
| 5,916,177 A | 6/1999 | Schwager | | 6,602,207 B1 | 8/2003 | Mann et al. |
| 5,916,178 A | 6/1999 | Noone | | 6,602,280 B2 | 8/2003 | Chobotov |
| 5,916,194 A | 6/1999 | Jacobsen et al. | | 6,610,046 B1 | 8/2003 | Usami et al. |
| 5,931,830 A | 8/1999 | Jacobsen et al. | | 6,623,448 B2 | 9/2003 | Slater |
| 5,935,108 A | 8/1999 | Katoh et al. | | 6,636,758 B2 | 10/2003 | Sanchez et al. |
| 5,947,940 A | 9/1999 | Beisel | | 6,638,266 B2 | 10/2003 | Wilson et al. |
| 5,951,539 A | 9/1999 | Nita et al. | | 6,652,508 B2 | 11/2003 | Griffin et al. |
| 5,971,975 A | 10/1999 | Mills et al. | | 6,682,493 B2 | 1/2004 | Mirigian |
| 5,980,471 A | 11/1999 | Jafari | | 6,689,120 B1 | 2/2004 | Gerdts |
| 6,001,068 A | 12/1999 | Uchino et al. | | 6,702,762 B2 | 3/2004 | Jafari et al. |
| 6,004,279 A | 12/1999 | Crowley et al. | | 6,712,826 B2 | 3/2004 | Lui |
| 6,014,919 A | 1/2000 | Jacobsen et al. | | 6,730,095 B2 | 5/2004 | Olson, Jr. et al. |
| 6,017,319 A | 1/2000 | Jacobsen et al. | | 6,749,560 B1 | 6/2004 | Konstorum et al. |
| 6,022,343 A | 2/2000 | Johnson et al. | | 6,766,720 B1 | 7/2004 | Jacobsen et al. |
| 6,022,369 A | 2/2000 | Jacobsen et al. | | 6,777,644 B2 | 8/2004 | Peacock, III et al. |
| 6,024,730 A * | 2/2000 | Pagan ........................... 604/264 | | 6,811,544 B2 | 11/2004 | Schaer |
| 6,027,461 A | 2/2000 | Walker et al. | | 6,837,898 B2 | 1/2005 | Boyle et al. |
| 6,042,553 A | 3/2000 | Solar et al. | | 6,866,642 B2 | 3/2005 | Kellerman et al. |
| 6,045,547 A | 4/2000 | Ren et al. | | 6,887,235 B2 | 5/2005 | O'Connor et al. |
| 6,048,339 A | 4/2000 | Zirps et al. | | 6,918,882 B2 | 7/2005 | Skujins et al. |
| 6,056,702 A | 5/2000 | Lorenzo | | 6,997,937 B2 | 2/2006 | Jacobsen et al. |
| 6,063,101 A | 5/2000 | Jacobsen et al. | | 7,001,369 B2 | 2/2006 | Griffin et al. |
| 6,063,200 A | 5/2000 | Jacobsen et al. | | 7,074,197 B2 | 7/2006 | Reynolds et al. |
| 6,066,361 A | 5/2000 | Jacobsen et al. | | 7,153,277 B2 | 12/2006 | Skujins et al. |
| 6,106,485 A | 8/2000 | McMahon | | 7,182,735 B2 | 2/2007 | Shireman et al. |
| 6,106,488 A | 8/2000 | Fleming et al. | | 2002/0013540 A1 | 1/2002 | Jacobsen et al. |
| 6,139,510 A | 10/2000 | Palermo | | 2002/0019599 A1 | 2/2002 | Rooney et al. |
| 6,159,187 A * | 12/2000 | Park et al. ..................... 604/264 | | 2003/0009208 A1 | 1/2003 | Snyder et al. |

| | | |
|---|---|---|
| 2003/0060732 A1 | 3/2003 | Jacobsen et al. |
| 2003/0069522 A1 | 4/2003 | Jacobsen et al. |
| 2003/0216668 A1 | 11/2003 | Howland et al. |
| 2004/0116831 A1 | 6/2004 | Vrba |
| 2004/0142643 A1 | 7/2004 | Miller et al. |
| 2004/0167436 A1 | 8/2004 | Reynolds et al. |
| 2004/0167437 A1 | 8/2004 | Sharrow et al. |
| 2004/0167441 A1 | 8/2004 | Reynolds et al. |
| 2004/0181174 A2 | 9/2004 | Davis et al. |
| 2004/0181176 A1 | 9/2004 | Jafari et al. |
| 2006/0121218 A1 | 6/2006 | Obara et al. |
| 2006/0122537 A1 | 6/2006 | Reynolds et al. |
| 2006/0189896 A1 | 8/2006 | Davis et al. |
| 2006/0264904 A1 | 11/2006 | Kerby et al. |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021404 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021407 A1 | 1/2008 | Jacobsen et al. |
| 2008/0021408 A1 | 1/2008 | Jacobsen et al. |

FOREIGN PATENT DOCUMENTS

| | | |
|---|---|---|
| BR | PI 9712829 | 1/2000 |
| CA | 2266685 | 5/2006 |
| CA | 2255781 | 3/2007 |
| CN | 1230914 | 10/1999 |
| DE | 2539191 | 3/1976 |
| DE | 285514 | 12/1990 |
| EP | 0 045 931 | 2/1982 |
| EP | 0 069 522 | 1/1983 |
| EP | 0 087 933 | 9/1983 |
| EP | 0 111 044 | 6/1984 |
| EP | 0 181 174 | 5/1986 |
| EP | 0 377 453 | 7/1990 |
| EP | 0 565 065 | 6/1996 |
| EP | 0 778 038 | 6/1997 |
| EP | 0 778 039 | 6/1997 |
| EP | 0 778 040 | 6/1997 |
| EP | 0 812 599 | 12/1997 |
| EP | 0 865 772 | 9/1998 |
| EP | 0 865 773 | 9/1998 |
| EP | 0 521 595 | 5/1999 |
| EP | 0 917 885 | 5/1999 |
| EP | 0 937 481 | 8/1999 |
| EP | 0 790 066 | 4/2000 |
| EP | 0 608 853 | 4/2003 |
| EP | 0 935 947 | 12/2004 |
| EP | 0 934 141 | 11/2005 |
| GB | 2214354 | 8/1989 |
| GB | 2257269 | 1/1993 |
| JP | 58-8522 | 1/1983 |
| JP | 60091858 | 5/1985 |
| JP | 61022752 | 1/1986 |
| JP | 62023361 | 1/1987 |
| JP | 62089470 | 4/1987 |
| JP | 62299277 | 12/1987 |
| JP | 6393516 | 4/1988 |
| JP | 63-181774 | 7/1988 |
| JP | 63217966 | 9/1988 |
| JP | 1089956 | 4/1989 |
| JP | 1135363 | 5/1989 |
| JP | 1158936 | 6/1989 |
| JP | 2107268 | 4/1990 |
| JP | 3081831 | 4/1991 |
| JP | 03-122850 | 12/1991 |
| JP | 4061840 | 2/1992 |
| JP | 4099963 | 3/1992 |
| JP | 4213069 | 8/1992 |
| JP | 4213070 | 8/1992 |
| JP | 4236965 | 8/1992 |
| JP | 5149969 | 6/1993 |
| JP | 5-506806 | 10/1993 |
| JP | 5-309159 | 11/1993 |
| JP | 5-507857 | 11/1993 |
| JP | 6-501179 | 2/1994 |
| JP | 631749 | 4/1994 |
| JP | 6169996 | 6/1994 |
| JP | 6-63224 | 9/1994 |
| JP | 6312313 | 11/1994 |
| JP | 728562 | 5/1995 |
| JP | 7124164 | 5/1995 |
| JP | 7124263 | 5/1995 |
| JP | 7136280 | 5/1995 |
| JP | 7148264 | 6/1995 |
| JP | 7505561 | 6/1995 |
| JP | 7037199 | 7/1995 |
| JP | 7185009 | 7/1995 |
| JP | 7255855 | 10/1995 |
| JP | 7275366 | 10/1995 |
| JP | 751067 | 11/1995 |
| JP | 8-229888 | 9/1996 |
| JP | 8509141 | 10/1996 |
| JP | 8317988 | 12/1996 |
| JP | 9000164 | 4/1997 |
| JP | 9-276413 | 10/1997 |
| JP | 9276413 | 10/1997 |
| JP | 9-294813 A | 11/1997 |
| JP | 9294813 | 11/1997 |
| JP | 10-118193 | 5/1998 |
| JP | 10328191 | 12/1998 |
| JP | 11-267224 A | 10/1999 |
| JP | 2000-197704 A | 7/2000 |
| JP | 2000-510722 A | 8/2000 |
| JP | 2000-511083 A | 8/2000 |
| JP | 2001-500808 A | 1/2001 |
| JP | 3325828 | 7/2002 |
| JP | 2002-529137 A | 9/2002 |
| JP | 2002-542901 A | 12/2002 |
| JP | 2002-543896 A | 12/2002 |
| JP | 2003-517893 A | 6/2003 |
| JP | 3649604 | 2/2005 |
| JP | 2005-534407 | 11/2005 |
| SU | 712908 | 1/1980 |
| SU | 758421 | 8/1980 |
| SU | 1529365 | 12/1989 |
| WO | WO 90/02520 | 3/1990 |
| WO | WO 91/13364 | 9/1991 |
| WO | WO 92/04072 | 3/1992 |
| WO | WO 92/07619 | 5/1992 |
| WO | WO 93/04722 | 3/1993 |
| WO | WO 93/11313 | 6/1993 |
| WO | WO 95/24236 | 9/1995 |
| WO | WO 96/19255 | 6/1996 |
| WO | WO 97/10022 | 3/1997 |
| WO | WO 97/25914 | 7/1997 |
| WO | WO 97/43949 | 11/1997 |
| WO | WO 97/44083 | 11/1997 |
| WO | WO 97/44086 | 11/1997 |
| WO | WO 98/10694 | 3/1998 |
| WO | WO 99/04847 | 2/1999 |
| WO | WO 99/11313 | 3/1999 |
| WO | WO 00/27303 | 5/2000 |
| WO | WO 00/30710 | 6/2000 |
| WO | WO 00/48645 | 8/2000 |
| WO | WO 00/57943 | 10/2000 |
| WO | WO 00/66199 | 11/2000 |
| WO | WO 00/67845 | 11/2000 |
| WO | WO 00/72907 | 12/2000 |
| WO | WO 01/28620 | 4/2001 |
| WO | WO 01/36034 | 5/2001 |
| WO | 0145912 | 6/2001 |
| WO | WO 01/45773 | 6/2001 |
| WO | WO 01/93920 | 12/2001 |
| WO | WO 02/13682 | 2/2002 |
| WO | WO 02/062540 | 8/2002 |
| WO | WO 03/004086 | 1/2003 |
| WO | WO 03/008148 | 1/2003 |
| WO | WO 2004/012804 | 2/2004 |
| WO | 2004047899 | 6/2004 |

* cited by examiner

TORQUEABLE SOFT TIP MEDICAL DEVICE AND METHOD OF USAGE

CROSS REFERENCE TO RELATED APPLICATIONS

This application is a continuation of U.S. application Ser. No. 10/188,929, filed Jul. 3, 2002; now abandoned which claims priority to U.S. Provisional Application Ser. No. 60/302,685, filed Jul. 5, 2001, the entire disclosures of which are incorporated herein by reference.

FIELD OF INVENTION

This invention relates generally to flexible medical devices and methods of using them.

BACKGROUND OF THE INVENTION

Medical devices such as endovascular or intravascular devices have been used for many years for purposes such as performing medical procedures, including treating aneurysms. A medical device such as an intravascular device may be introduced into a patient's anatomy or vasculature at a relatively accessible location, and guided through the patient's anatomy to the desired location. X-ray fluoroscopy has been used to observe the tip of the medical device and the device has been rotated at bifurcations in the anatomy or vasculature before being pushed further to guide the device to the desired location. Medical devices of this type may be solid, for example, a guide wire, or may be hollow and tubular, for example, a catheter. Guide wires may be used to guide one or more tubular intravascular devices to a particular location, and catheters may be used, for instance, to deliver fluids, extract fluids, or deliver various objects, agents, or devices to the particular location.

In many applications it is desirable that a medical device or intravascular device bend easily in order to allow it to make the various bends and turns that are necessary to navigate through the anatomy or vasculature, and in some cases also to minimize trauma to the anatomy or vasculature. However, in many applications it is desirable that the medical device be relatively stiff in torsion in order to allow precise control of rotation in order to guide the device through bifurcations in vasculature or around obstacles. Accordingly, medical and intravascular devices have been described that contain numerous cuts along their length to obtain the desired flexibility in bending while maintaining relative stiffness in torsion. Examples of such devices are described in U.S. Pat. Nos. 5,690,120 and 5,833,632, both of which are incorporated herein by reference in their entirety. An example of a method of making such devices is described in U.S. Pat. No. 6,260,485 B1, which is also incorporated herein by reference in its entirety.

In many applications, it is desirable that the tip of a medical device be soft and bendable so as to minimize trauma to the patient's anatomy and further facilitate negotiating bends and turns in the anatomy or vasculature. Thus, a need exists for such a soft and bendable tip. In addition, the tip of a medical device may be bent or curved so that when the device approaches a bifurcation, or other location where direction needs to be selected, the device may be steered in the correct direction. In the past, tips were bent or curved during initial fabrication of the device. However, in at least some applications, a greater or lesser curvature may be desirable. Accordingly, a need exists for a device wherein the angle or radius of bending or curvature of the tip may be selected by the operator of the medical device, for instance, by the medical doctor performing a medical procedure with the medical device.

Furthermore, in many applications, it is desirable and important that the entire device be removed after the procedure is completed. Thus, it is desirable that the device have a strong and reliable tensile strength throughout its length so that it does not come apart when pulled out of the patient's anatomy or vasculature. Accordingly, a need exists to improve and provide redundancy in the tensile strength of a medical device to assure complete removal of the device.

SUMMARY OF THE INVENTION

The present invention provides medical devices including intravascular devices and methods of using medical devices and intravascular devices. Medical devices in accordance with the present invention may be, for example, a guide wire that may be hollow. Features and objects of various embodiments of the present invention include that the devices are flexible in bending, the devices and methods minimize trauma to the patient's anatomy, and the devices and methods assure complete removal of the medical device.

Accordingly, in at least partial fulfillment of these objects, an exemplary embodiment of the present invention includes a medical device that may be an intravascular device, that has a body with a proximal end and a distal end. The body may have a plurality of cuts part way through. The device may also have a tip extending from the distal end of the body, which may be substantially made of a non-metallic material. The tip may be more flexible in bending than the body, and may be configured to be custom shaped by the person who will operate the device. The body may be substantially comprised of metal, which may be super-elastic nitinol. The body may be substantially tubular, and may have at least one substantially tubular liner. The liner may extend from the proximal end of the body to the distal end of the body, and may further extend distal to the body. In some embodiments, the liner may be inside the body and extend through the body, and in some embodiments may further extend through the tip. In some embodiments, the tip may be essentially the distal end of the liner. In other embodiments, the tip may further have a tubular end sleeve, which may be substantially comprised of polymer. The tip may also have an anti-collapsing structure, which may be a groove, a coil, or a braid. The device may also have at least one marker. Some embodiments of the present invention include a fiber extending through the body, which may be configured to increase the device's tensile strength. The fiber may be substantially comprised of a high-strength material, and may zigzag between the body and the liner.

A further exemplary embodiment of the present invention includes a method of treating a patient with a medical device. The method may include the steps of selecting a medical device, which may have a flexible tip; shaping the tip, for instance by bending it; and inserting the device into the anatomy or vasculature. The step of inserting the device may include axially translating the device, rotating the device, and monitoring the distal end or tip. The tip may be made of a non-metallic material and may have at least one marker to facilitate monitoring by observing it, for instance, with X-ray fluoroscopy. The method may also have the step, after the step of shaping, of setting the shape of the tip, for example, by heating the tip. The device may be substantially tubular, and the method may also include the step, after the step of shaping, of removing a mandrel from the tip that had been previously inserted. After the device is inserted into the anatomy or vasculature, the method may include the step of performing a medical procedure using the device, for example, treating an aneurysm. The method may further include the step of removing the device, which may involve using a fiber running substantially through the device. The fiber may accordingly be configured to assure complete removal of the device.

BRIEF DESCRIPTION OF THE DRAWINGS

The figures in this document illustrate various exemplary embodiments of the present invention. Embodiments of the present invention may include part or all of the features shown in one of these drawings, or may include features from two or more figures. Embodiments of the present invention may also include features described in the specification, or limitations to features described in the specification. Furthermore, embodiments of the present invention may include features that would be familiar to a person of ordinary skill in the art having studied this document.

DETAILED DESCRIPTION

The present invention provides medical devices and intravascular devices such as hollow guide wires, and methods of using medical devices and intravascular devices. Exemplary embodiments of medical devices in accordance with the present invention may be flexible in bending, minimize trauma to the patient's anatomy or vasculature, assure complete removal of the medical device, or provide a combination of these features. Other features may also be provided.

Figures 1, 2, 3:
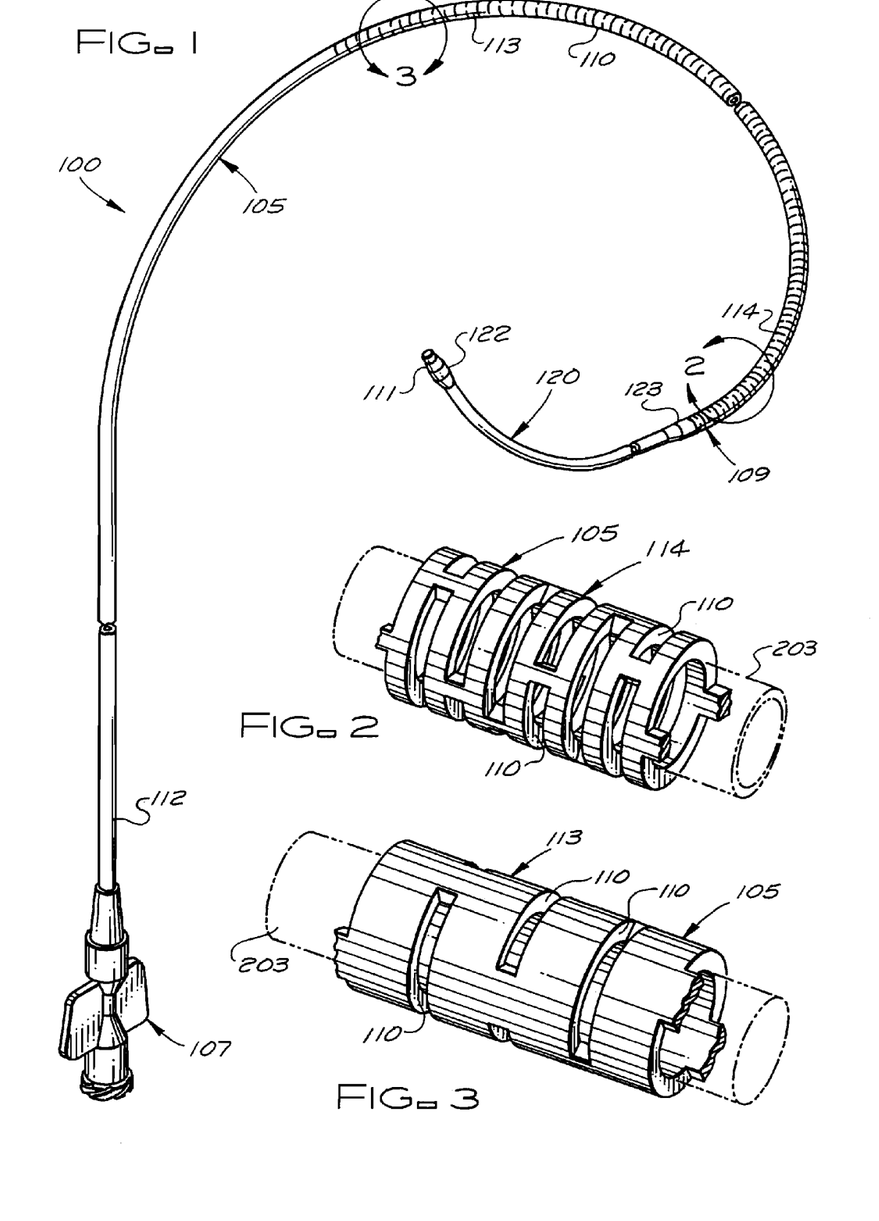
FIG. 1 is a side view illustrating an embodiment of a medical device in accordance with the present invention.
FIG. 2 is a detail isometric view illustrating a portion of the body and liner of the medical device illustrated in FIG. 1.
FIG. 3 is a detail isometric view illustrating another portion of the body and liner of the medical device illustrated in FIG. 1.
Figure 4:
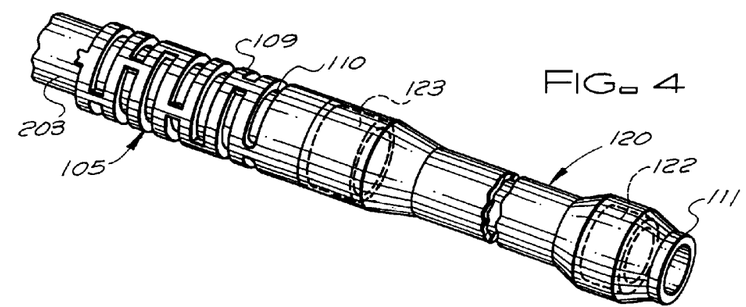
FIG. 4 is an isometric view showing an exemplary embodiment of the tip of a medical device in accordance with the present invention.

Accordingly, FIG. 1 illustrates an embodiment of a medical device 100 in accordance with the present invention that includes a body 105 that has a proximal end 107, a distal end 109, and an axis (longitudinal axis) extending through the proximal end 107 and the distal end 109. Medical device 100 may be, for example, an endovascular or intravascular device. The body 105 may have a plurality of cuts 110 (one of which is labeled 110 on FIG. 1) part way through the body 105, and the cuts 110 may be approximately or substantially perpendicular to the axis. The body 105 may have a portion 112 without any cuts 110, a portion 113 with cuts 110 relatively far apart, and a portion 114 with cuts 110 relatively close together. Exemplary embodiments of portions 113, and 114, and cuts 110 are illustrated in more detail in FIGS. 2 and 3. Cuts 110 may be saw cut, notched, laser cut, ground, EDMed, etched, forged, molded, or formed by another method suitable for shaping the material from which body 105 is made. The geometry of cuts 110 may be as shown, or in various embodiments may be of other geometries forming openings through the wall of body 105. Returning to FIG. 1, the spacing of cuts 110 may vary gradually from portion 113 to portion 114, or the spacing may vary discreetly. In some embodiments, the spacing of cuts 110 may be substantially uniform throughout all or part of body 105. In some embodiments, the geometry of cuts 110 may vary, for example, in width (in the direction of the axis of body 105) or depth.

Still referring to FIG. 1, medical device 100 may further include a tip 120 on the distal end of medical device 100, which may extend from the distal end 109 of body 105. As will be described in further detail below, tip 120 may substantially comprise one or more non-metallic materials, for example, a polymer material. Due in some embodiments to the properties of the material from which it is made, its dimensions, or both, tip 120 may be more flexible in bending than body 105. In other words, tip 120 may be a flexible tip. In addition, as will be described in more detail below, tip 120 may be configured to be custom shaped by the person who will operate the device 100, for example, to perform a medical procedure. Tip 120 may have its own distal end 111, for example on the far distal end of device 100. Tip 120 may be marked, for example, on the distal end 111 of tip 120, for example, with a marker band, or other indication. The presence of this marking or indication may be checked upon removal of device 100 from the patient to verify that all of device 100 has been completely removed. Tip 120 may be flared at distal end 111, for example, on the inside, or may be rounded, for example to minimize trauma to the anatomy or vasculature.

Referring to FIGS. 2 and 3, body 105 may be substantially comprised of metal, which may be a nickel-titanium alloy (nitinol). The nitinol may be a super-elastic nitinol, meaning its transition temperature may be below the use temperature. In many embodiments of the present invention, the use temperature may be human body temperature or room temperature. In other embodiments, body 105 may be a polymer material or stainless steel, or another material suitable for the application. Body 105 may be substantially tubular as shown, or in some embodiments, may be solid. Medical device 100 may further comprise a substantially tubular liner 203, which may extend the length of body 105, for example from proximal end 107 at least to distal end 109. Liner 203 may be located inside body 105 (as shown) or may be located outside body 105. Liner 203 may be located inside body 105, for example, to make the inside of device 100 smoother to reduce friction or abrasiveness, for example, for passing objects through the interior of device 100. Liner 203 may be located outside body 105, for example, to make the outside of device 100 smoother to reduce friction, abrasiveness, and trauma to the anatomy or vasculature. Some embodiments of the present invention may have two liners 203, one inside body 105 and one outside body 105.

Figure 7:
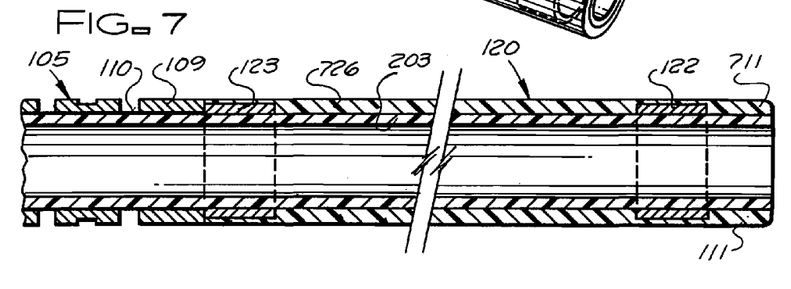
FIG. 7 is a sectional side view further illustrating the exemplary embodiment of the tip of the medical device shown in FIG. 6, illustrating, among other things, an end sleeve.

Liner 203 may lack many or all of the cuts 110 of body 105, thus forming a barrier that may reduce or eliminate leakage between the interior and exterior of body 105. In other words, liner 203 may seal cuts 110. Liner 203 may be made of an elastomeric material. Liner 203 may be made of a polymer, such as a polyethylene blend, or PTFE. Liner 203 may further extend distal to body 105 (for example beyond distal end 109), for example, through tip 120, and, as illustrated best in FIG. 5, in some embodiments, may substantially comprise or form tip 120. As used herein, tip 120 substantially comprises liner 203 in embodiments where tip 120 is comprised of part of liner 203, but tip 120 does not include a separate end sleeve 726 (illustrated in FIG. 7). As used herein, the statement that tip 120 substantially comprises liner 203 does not mean that tip 120 does not have markers 122 and 123, or an anti-collapsing structure (e.g. coil 1032 or braid 1333) (described below).

End sleeve 726 may be substantially tubular and is illustrated in FIGS. 6-13, and is a component of some embodiments of medical device 100. End sleeve 726 may have the same or a similar inside and outside diameter as distal end 109 of body 105 (illustrated best in FIG. 7), and may substantially comprise a polymer material. End Sleeve 726 may, for example, be a lamination of PEBAX, for instance, and may have a durometer hardness of 85 A. Various hardnesses may be preferred for various applications and embodiments. End sleeve 726 may, in some embodiments, be attached to body 105, for example, with an adhesive. In some embodiments of tip 120, liner 203 and end sleeve 726 may be attached to each other, for example with an adhesive (e.g. cyanoacrylate), or may not be attached to each other, e.g. to promote flexibility of tip 120. Embodiments having two liners 203 (for example, a first liner 203 inside the body and a second liner 203 outside the body) may have an end sleeve 726 disposed between the two liners 203. In embodiments with either one or more liners, the end sleeve 726 may extend beyond (distal to) the end or ends of one or more liners 203. In other words, one or more liners 203 may terminate substantially proximal to the distal end 711 of end sleeve 726. As used here, substantially proximal means at least 10 percent of the length of tip 120 from the distal end 711 of end sleeve 726.

Figures 10, 11:
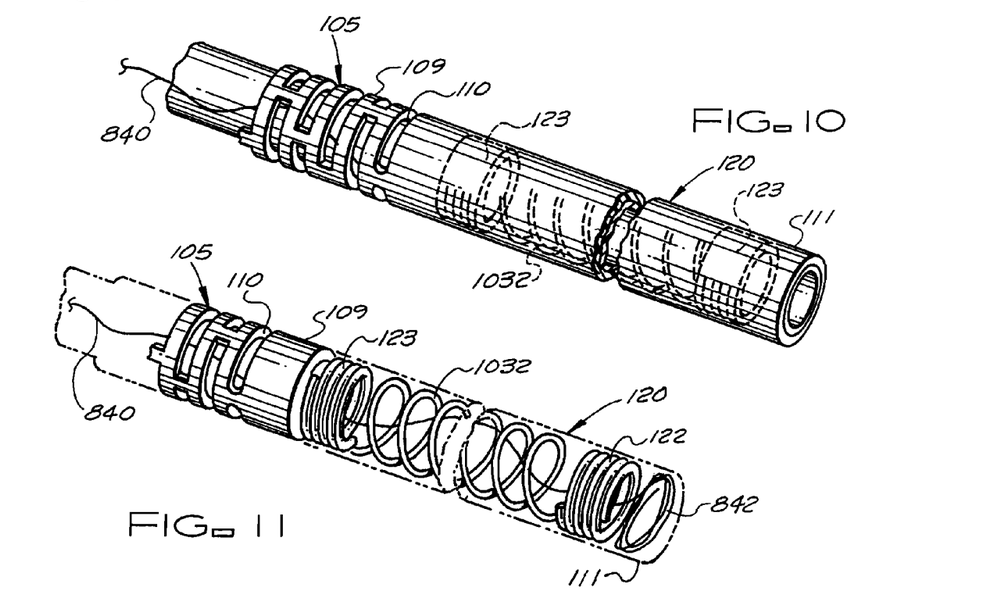
FIG. 10 is an isometric view showing an exemplary embodiment of an anti-collapsing structure and markers that may be part of the tip of a medical device in accordance with the present invention.
FIG. 11 is an isometric view showing another exemplary embodiment of an anti-collapsing structure and markers that may be part of the tip of a medical device in accordance with the present invention.
Figure 12:
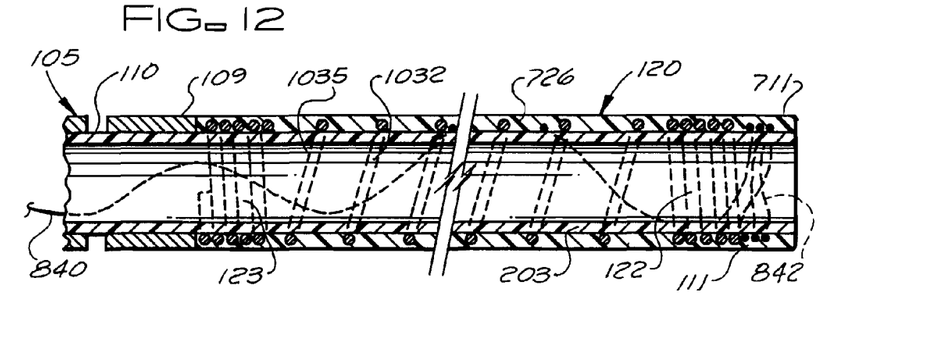
FIG. 12 is a sectional side view further illustrating the anti-collapsing structure and markers shown in FIG. 11.
Figures 13, 18, 19, 20:
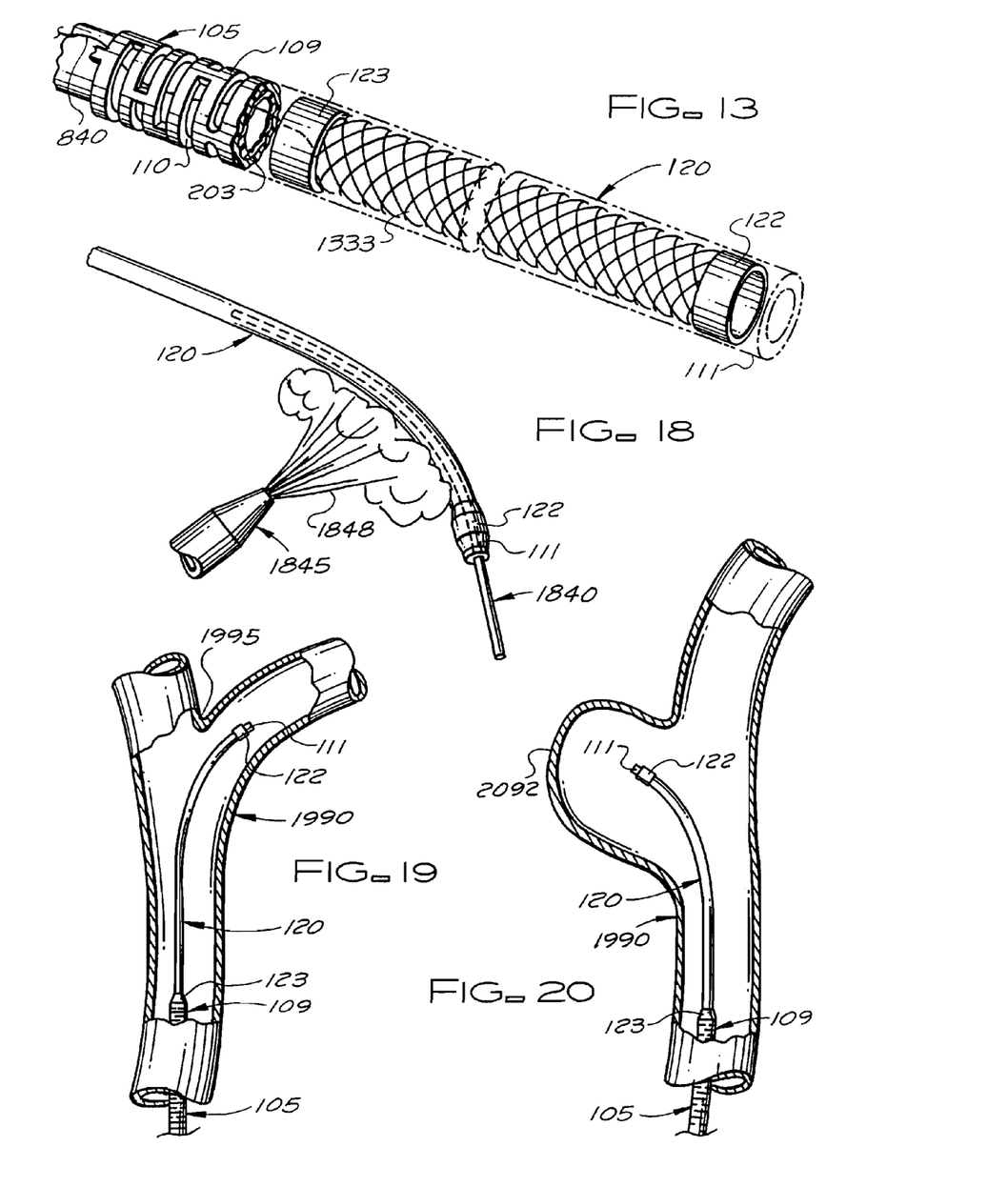
FIG. 13 is an isometric view showing another exemplary embodiment of an anti-collapsing structure and markers that may be part of the tip of a medical device in accordance with the present invention.
FIG. 18 is a side view illustrating setting the tip of an exemplary embodiment of the present invention.
FIG. 19 is a cut-a-way side view illustrating using the bend in the tip of a medical device in accordance with an exemplary embodiment of the present invention to facilitate navigation through a bifurcation in vasculature.
FIG. 20 is a cut-a-way side view illustrating using the bend in the tip of a medical device in accordance with an exemplary embodiment of the present invention to treat an aneurysm.

As illustrated in FIGS. 10-13, tip 120 of medical device 100 may further comprise an anti-collapsing structure, which may be coil 1032 as illustrated in FIGS. 10-12 or braid 1333 as illustrated in FIG. 13. The anti-collapsing structure (e.g. coil 1032 or braid 1333) may be located between liner 203 and end sleeve 726 a illustrated best in FIG. 12. In some embodiments, the anti-collapsing structure may be one or more grooves 1035 as illustrated in FIG. 12. Groove 1035 may be a helical groove (shown), or may be a plurality of circular grooves, for example circumferential to the axis of body 105 or medical device 100. Groove 1035 may be cut in part of tip 120, for example, liner 203 or end sleeve 726 (shown). Groove 1035 may be cut on the inside (shown) or the outside, depending on the embodiment. As would be apparent to a person skilled in the art, the outside may be more accessible for cutting groove 1035, particularly in smaller diameter embodiments of device 100. Coil 1032 may be located inside groove 1035 (for example, where groove 1035 is helical). In other embodiments, groove 1035 may be hollow or may contain another component or material. For example, in embodiments having a plurality of circumferential grooves 1035, rings may be disposed in grooves 1035, e.g. rings comprised of a metal or polymer, which may have a substantially higher stiffness (e.g., modulus of elasticity) than liner 203 or end sleeve 726.

Figure 5:
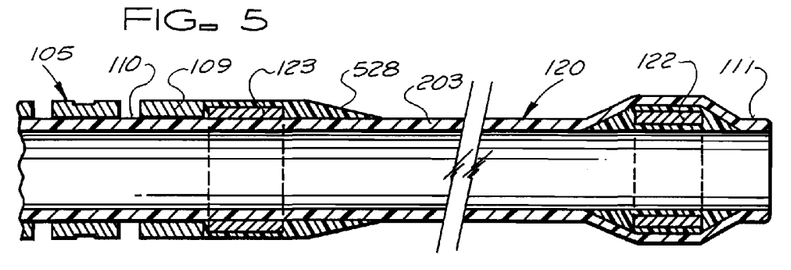
FIG. 5 is a sectional side view further illustrating the exemplary embodiment of the tip of the medical device shown in FIG. 4, illustrating the tip substantially comprising the liner.
Figure 6:
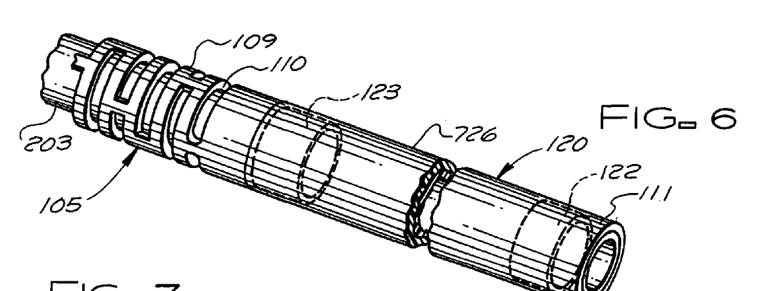
FIG. 6 is an isometric view showing another exemplary embodiment of the tip of a medical device in accordance with the present invention.

Medical device 100 may comprise at least one tip marker 122 or 123 as illustrated in FIGS. 1 and 4-20. As illustrated, many embodiments include two markers, marker 122 at the distal end 111 of tip 120 and marker 123 at the base of tip 120, for example, near distal end 109 of body 105. As used herein, the statement that tip 120 substantially comprises a non-metallic material means, for example, that liner 203 and exterior portion 726 (in embodiments where provided) are not made of metal, but markers 122 and 123, and anti-collapsing structure (e.g. coil 1032 or braid 1333) may be any material including a metal. Markers 122 and 123 may be made of a material such as platinum that is readily distinguishable with X-ray fluoroscopy. Markers 122 and 123 may be short tubular sleeves or bands as illustrated in FIGS. 4-10, 13, 14, and 16, or may be coils as illustrated in FIGS. 11, 12, 15, and 17. In some embodiments having an anti-collapsing structure that is a coil 1032, markers 122, 123, or both, may be formed from the same wire as coil 1032, and may be integral therewith. For illustration, see FIG. 11. In other embodiments, markers 122 and 123 may be coils but may be separate components from coil 1032. The coils of markers 122 and 123 may be closer together (i.e. in the axial direction) than the coils of coil 1032 as shown. The coils of markers 122 and 123 may, in fact, be touching each other or nearly touching. The markers 122 and 123 may be located between liner 203 and end sleeve 726 as illustrated best in FIGS. 7, 9, and 12. Markers 122 and 123 may be covered all or in part by a material 528 (as illustrated best in FIG. 5 for marker 123) that may be smooth, soft, slippery, or some combination thereof to minimize trauma to the patient's anatomy or vasculature 1990. Material 528 may be an adhesive, for example, a UV adhesive. In some embodiments, for example, not having an end sleeve 726, markers 122 and 123 may be located inside liner 203 (as illustrated in FIG. 5 for marker 122).

Figure 14:
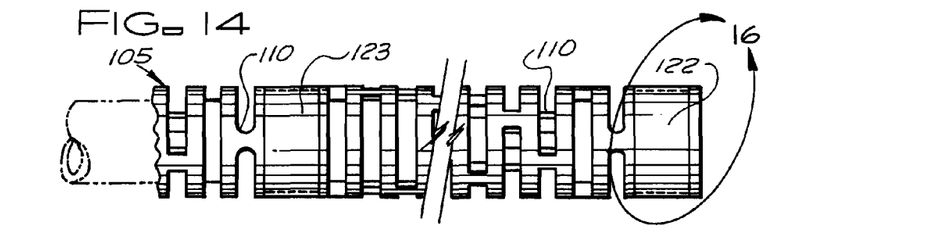
FIG. 14 is a side view illustrating an embodiment of markers in accordance with the present invention.
Figure 15:
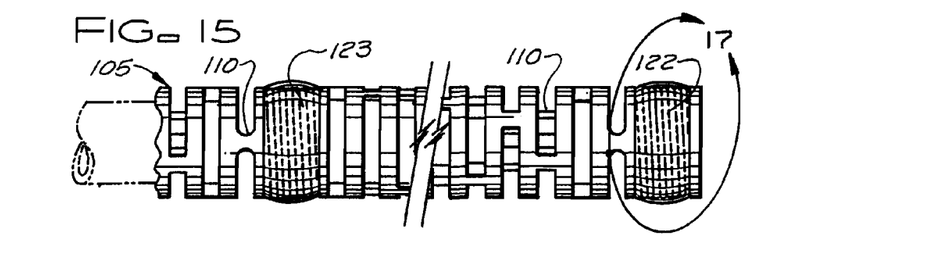
FIG. 15 is a side view illustrating another embodiment of markers in accordance with the present invention.
Figure 16:
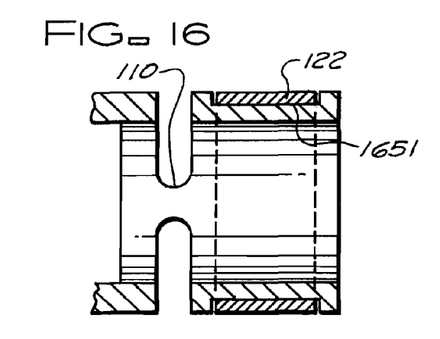
FIG. 16 is a detail sectional side view showing the embodiment of markers illustrated in FIG. 14.
Figure 17:
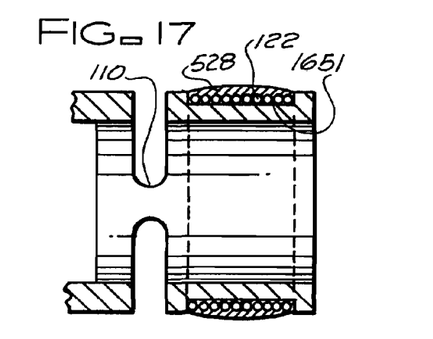
FIG. 17 is a detail sectional side view showing the embodiment of markers illustrated in FIG. 15.

There may be an interference fit between marker 122 or 123 and liner 203. And, there may be an interference fit between marker 122 or 123 and end sleeve 726. Such interference fits may hold markers 122 and 123 in place. Markers 122 and 123 may also be held in place with an adhesive, or may be thermally fused, i.e. by melting a polymer such as a thermal plastic around marker 122 or 123. Material 528 shown in FIG. 5, for example, may be an adhesive or a polymer. In some embodiments, markers 122, 123, or both may be recessed in a groove 1651 as illustrated in FIGS. 14-17. Groove 1651 may be cut, for example, in body 105 as shown, but may alternatively be cut in liner 203 or end sleeve 726, for further example. Markers 122 and 123 may be short cylinders or sleeves as illustrated in FIGS. 14 and 16, which may be crimped or swaged into groove 1651. In another embodiment, illustrated in FIGS. 15 and 17, markers 122 and 123 may be coils, which may be expanded to install them in groove 1651. Markers 122 and 123 may be covered with a material 528 as described above and as illustrated in FIGS. 15 and 17 to help hold markers 122 and 123 in place or to minimize trauma to the patient's anatomy or vasculature 1990.

As illustrated in FIGS. 8-13, medical device 100 may have a fiber 840 extending through body 105. Fiber 840 may be configured to provide tensile strength (for example, redundant tensile strength) to medical device 100 or increase its tensile strength, for example, to assure complete removal of device 100 from the patient. As used herein, being configured to increase the tensile strength of device 100 includes increasing device 100's ultimate tensile strength, and providing redundancy in the tensile strength of device 100, for example, in case body 105, liner 203, or another component or joint has less tensile strength than anticipated. Thus, in some embodiments, fiber 840 may have a greater tensile strength than the remainder of medical device 100, but in other embodiments fiber 840 may have a lower tensile strength than a properly manufactured and undamaged device 100. Fiber 840 may substantially comprise a material selected for its high tensile strength. Fiber 840 may be a polymer, a metal, a carbon fiber, a ceramic fiber, or a combination of fibers. Fiber 840 may be formed from a composite material, and the fibers of the composite material may be substantially aligned in the axial direction of fiber 840. Fiber 840 may, for example, be made of KEVLAR.

Figure 8:
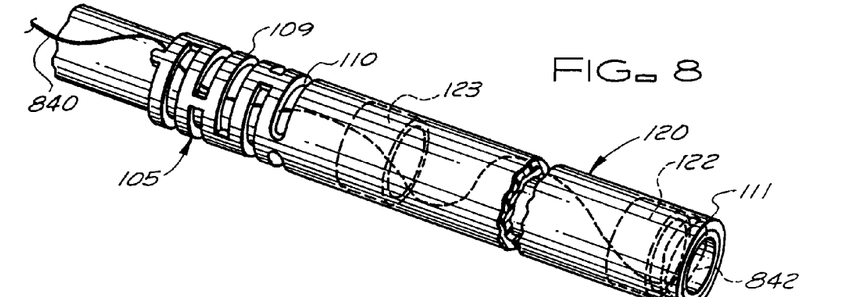
FIG. 8 is an isometric view showing additional features that may be part of the tip of the medical device shown in FIG. 6, including a fiber.
Figure 9:
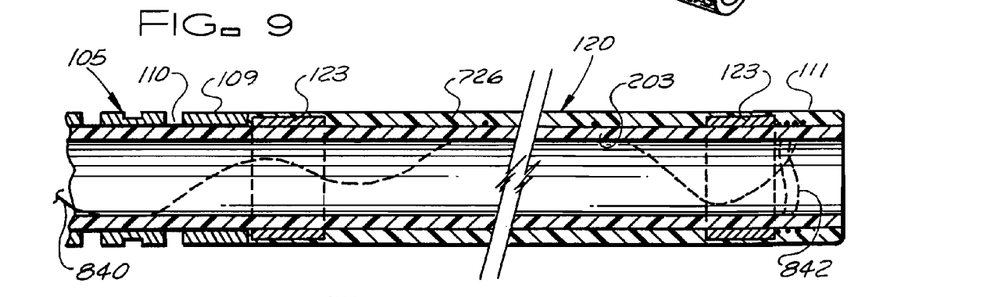
FIG. 9 is a sectional side view further illustrating the additional features shown in FIG. 8.

Fiber 840 may be located between body 105 and liner 203, and may bend back and forth or zigzag, for example in a somewhat sinusoidal pattern, be bunched, or wound in a spiral, so as to avoid or minimize increasing the bending stiffness of medical device 100 or maintain symmetrical bending properties of medical device 100 around its longitudinal axis. For example, fiber may zigzag back and forth over approximately ½ of the diameter of device 100. This zigzag pattern may, for instance, continue along one side of device 100, or may gradually spiral around device 100. Fiber 840 may wind (for example winds 842) around at least part of the components of tip 120, for instance, to help secure tip 120 to fiber 840. For example, fiber 840 may wind (winds 842) around liner 203 (shown) or end sleeve 726. Fiber 840 may be secured, for instance, to tip 120, for example, by being glued, twisted, or tied. Some embodiments may have a plurality of fibers 840. For example, in one embodiment device 100 may have two fibers 840 that may zigzag, for example, on opposite sides, or may spiral in opposite directions.

Various dimensions of tip 120 may be desirable for various embodiments of the present invention. Specifically, in various embodiments, tip 120 may be from as little as 1 millimeter in length to as long as 1500 millimeters in length. Other embodiments may even be outside of this range. Shorter lengths (e.g. as short as 1 millimeter long) may, for example, provide a soft tip 120 for medical device 100, which may reduce trauma to the patient's anatomy, for example, compared with having no tip 120 at all. Longer tips 120 may offer the other advantages described herein. Some embodiments of the present invention may have a tip 120 that is 10 to 40 millimeters long. For instance, embodiments of the present invention may have a tip 120 that is 31 millimeters long, and markers 122 and 123 may be 30 millimeters apart on embodiments having such markers. Such lengths may offer the various features and advantages described herein.

In addition, various outside diameters of medical device 100 may be desirable for various embodiments of the present invention. Generally, body 105 may have an outside diameter in the range of 0.010 to 0.500 inches. Other embodiments may even be outside of this range. For instance, some embodiments may be larger in diameter. However, within the range identified, some embodiments of the present invention may have a body with an outside diameter in the range of 0.030 to 0.040 inches. For example, embodiments of the present invention may have a body 105 with an outside diameter of 0.033 inches. Other embodiments may have a body with an outside diameter in the range of 0.020 to 0.040 inches. Still other embodiments may have a body with an outside diameter in the range of 0.015 to 0.040 inches. In some embodiments, the diameter of body 105 may vary along its length, for example, with the largest diameter at the proximal end 107 and the smallest diameter at the distal end 109. The outside diameter of tip 120 may be similar or less than the outside diameter of body 105, for instance, 0.033 inches.

Furthermore, various lengths of medical device 100 may be desirable for various embodiments of the present invention. Medical device 100 may be, for example, 155 centimeters long. Referring to FIG. 1, portions 112 and 113 with cuts 110, and tip 120, may total, for example, 48 centimeters long.

Figure 21:
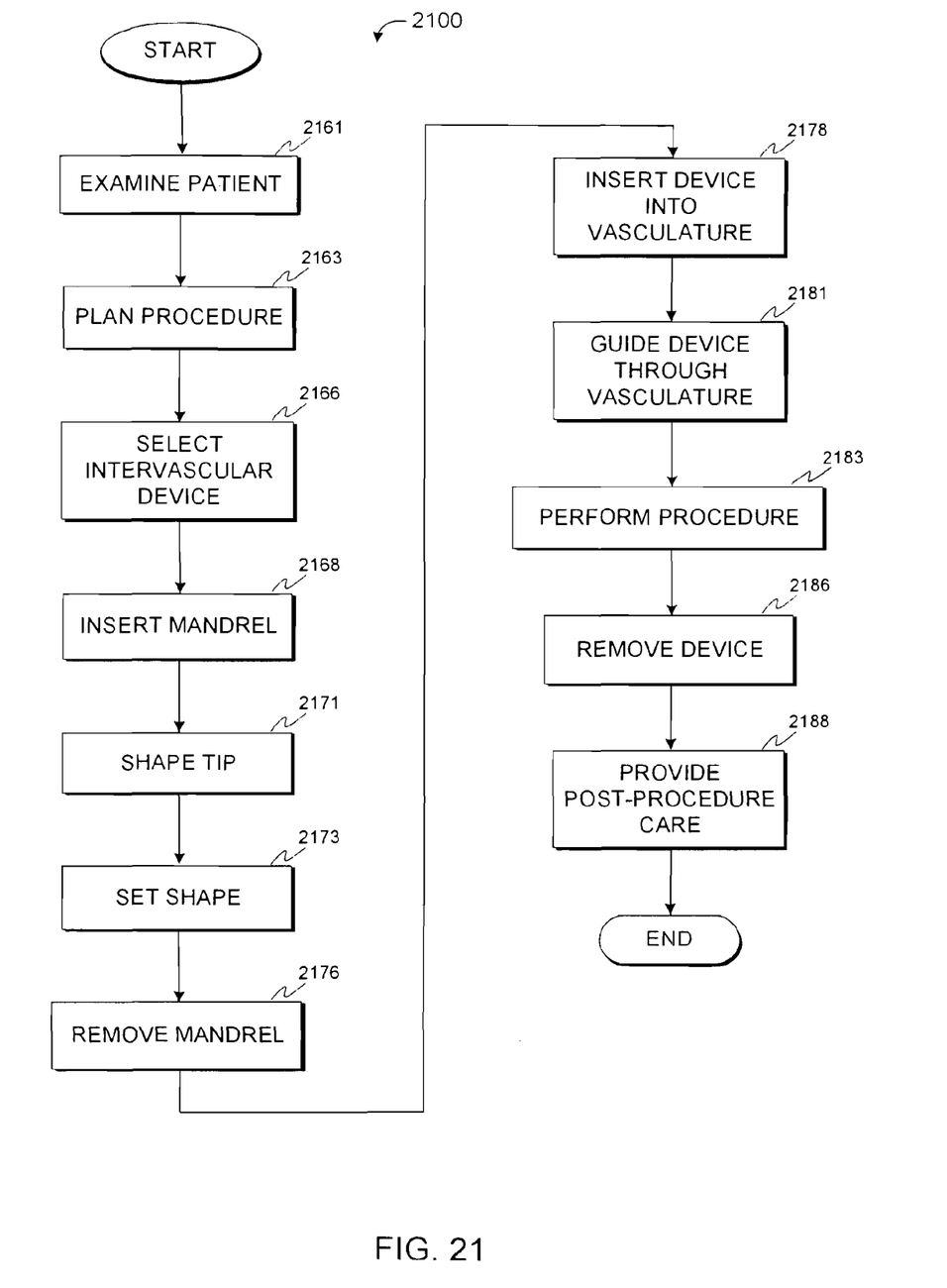
FIG. 21 is a flow chart illustrating steps of an exemplary embodiment of a method in accordance with the present invention.

Turning now to methods of using, for example, medical device 100, FIG. 18 illustrates how tip 120 of medical device 100 may be set in shape with steam 1848 and mandrel 1840 prior to using medical device 100. FIG. 19 illustrates how the shape or curvature of tip 120 may be used to navigate medical device 100 through a bifurcation 1995 in the patient's anatomy or vasculature 1990. FIG. 20 further illustrates how the shape or curvature of tip 120 may be used to treat an aneurysm 2092 in the patient's vasculature 1990. Even further, FIG. 21 illustrates various steps of an exemplary embodiment of a method in accordance with the present invention, method 2100.

Method 2100 illustrates a method of treating a patient with a medical device (e.g. device 100). First, the physician, for example, may examine the patient (step 2161) to determine what the problem is (e.g. an aneurysm) and plan the procedure (step 2163), for example, to correct the problem. Method 2100 then generally includes the step of selecting a medical device (step 2166), which may have various attributes of medical device 100, described above such as having a tip 120 or cuts 110. Selecting medical device 100 may include, for example, choosing the desired diameter and length of device 100. Various other features may be selected, including those features and embodiments described herein. Method 2100 also includes shaping (step 2171) tip 120, which may comprise bending tip 120; and inserting (step 2178) medical device 100 into anatomy or vasculature 1990. Then the physician or operator may guide (step 2181) the device 100 through the anatomy or vasculature (e.g. 1990). Inserting (step 2178) or guiding (step 2181) may comprise axially translating medical device 100, rotating medical device 100, and monitoring the distal end 109 or tip 120 (e.g. distal end 111) of medical device 100. For example, as illustrated in FIG. 19, when medical device 100 approaches a bifurcation 1995, for instance, in vasculature 1990, the operator may rotate the proximal end 107 (shown in FIG. 1) of device 100 while monitoring or observing marker 122 on distal end 111 of tip 120, and possibly also marker 123, for example, with an X-ray viewer. When marker 122, and thus distal end of device 100 and tip 120 (distal end 111), is pointed toward the desired passageway of vasculature 1990, the operator may then push medical device 100 further into vasculature 1990 so that tip 120 goes into the desired passageway.

Method 2100 may further comprise the-step, after shaping tip 120 (step 2171), of setting (step 2173) the shape of tip 120. Setting (step 2173) the shape may comprise heating tip 120, as illustrated in FIG. 18. Medical device 100 may be substantially tubular, and method 2100 may further comprise the step, after shaping tip 120 (step 2171), of removing (step 2176) a mandrel 1840 from tip 120. Thus, tip 120 may be shaped (step 2171) by bending tip 120 while a mandrel 1840 is inside tip 120. The mandrel 1840, which may be wire, for example, stainless steel, will then hold the shape of tip 120 while tip 120 is heated, for instance, with steam 1848 produced by steam source 1845. Thus, the operator or physician who is about to perform the medical procedure (step 2183) with medical device 100, may bend (step 2171) tip 120 based on the shape needed for the particular procedure and the patient's particular anatomy. The physician may then set the shape (step 2173) by heating tip 120 with a steam source 1845 that may be readily available. Then the physician may remove mandrel 1840 (step 2176), leaving tip 120 with the desired shape, but flexible. Mandrel 1840 may have been inserted (step 2168) by the physician, or may have been inserted by the manufacturer of device 100 before shipment to the physician.

Method 2100 may further comprise the step, after inserting medical device 100 into the anatomy or vasculature 1990 (step 2178), of performing a medical procedure step 2183) using medical device 100. The medical procedure (of step 2183) may be, for example, treatment of aneurisms, AVMs, bleeds, tumors, embolisms, embolic stroke thrombolysis, and thrombolectomy. In an exemplary embodiment, the procedure (of step 2183) may include treating an aneurysm 2092 as illustrated in FIG. 20, for example, a cerebral or brain aneurysm Such a treatment may involve, for example, introduction of an agent such as a glue material through device 100, stenting, installation of a graft, or balloon immobilization. Other procedures (of step 2183) may include obtaining access to the uterus, fallopian tubes, urinary tract, sinuses, esophagus, lungs, vertebroplasty, and gastroenterology. A gradual curvature of tip 120 is shown in FIG. 20, however, tip 120 may be shaped in radial bends, for example from 5 degrees to 120 degrees or in other complex shapes as needed by the physician. The length of tip 120 extending distal to the bend may be selected based on the size of the aneurysm 2092, the size of the vasculature 1990, and other factors.

Method 2100, may further comprise the step of removing medical device 100 (step 2186). This may involve using fiber 840 described above, for example, running substantially through medical device 100. To remove medial device 100, the operator or physician may pull on the proximal end 107 of medical device 100. If medical device 100 should pull apart or break, for example, tip 120 should separate from body 105, then fiber 840 may be utilized to facilitate or assure complete removal of medical device 100, including tip 120. To do so, the operator or physician may continue pulling on proximal end 107. After the slack is taken up from fiber 840, fiber 840 will then pull on tip 120. Accordingly, Fiber 840 may be configured to facilitate or assure complete removal of medical device 100. The physician may also provide post-procedure care (step 2188) to the patient, for example, verifying that the problem is corrected and that no complications have developed.

The above embodiments are illustrative of the present invention, but are not intended to limit its scope. Numerous modifications and alternative arrangements may be devised by those skilled in the art without departing from the spirit and scope of the present invention, and the appended claims are intended to cover such modifications and arrangements.

What is claimed is:

1. A catheter, comprising:
   an elongate shaft having a proximal section and a distal section;
   wherein the shaft includes an inner surface defining a lumen;
   wherein a plurality of slots are formed in the distal section;
   an elongate liner disposed in the shaft along the inner surface, wherein a distal portion of the liner extends distally from the distal section of the shaft; and
   wherein the distal portion of the liner deflects radially outward to define a flared tip with an enlarged section that includes a radiopaque marker band.

2. The catheter of claim 1, further comprising a second liner disposed on an outer surface of the shaft.

3. The catheter of claim 1, wherein the slots extend part way through the shaft.

4. The catheter of claim 1, wherein the tip member is shapeable.

5. The catheter of claim 1, wherein the distal portion of the liner has a length and wherein the tip member extends along the entire length of the distal portion.

6. The catheter of claim 1, wherein the tip member is more flexible in bending than the distal section of the shaft.

\* \* \* \* \*